United States Patent [19]

Hovatter

[11] Patent Number: 5,354,539
[45] Date of Patent: Oct. 11, 1994

[54] MICROTUBE HAVING PRESS-TO-SEAL AND TWIST-TO-LOCK CLOSURE CAP

[76] Inventor: Kenneth R. Hovatter, 1901 Ackerman Dr., Lodi, Calif. 95240

[21] Appl. No.: 150,716

[22] Filed: Nov. 12, 1993

[51] Int. Cl.$^5$ .................................. B01L 3/00
[52] U.S. Cl. ........................... 422/102; 220/306; 220/331; 220/339; 215/237
[58] Field of Search .............. 422/99, 102, 103; 435/296, 298; 220/306, 329, 331, 324, 339; 215/237, 216, 354, 322, 329, 336; 292/80, 87, 198, DIG. 38

[56] References Cited

U.S. PATENT DOCUMENTS

| | | | |
|---|---|---|---|
| 3,593,909 | 7/1971 | Bergmann | 229/43 |
| 3,651,992 | 3/1972 | Hazard | 222/153 |
| 3,986,627 | 10/1976 | Zapp | 215/237 |
| 4,158,902 | 6/1979 | Chernack et al. | 16/150 |
| 4,209,100 | 6/1980 | Uhlig | 215/216 |
| 4,241,188 | 12/1980 | Materia et al. | 435/296 |
| 4,244,920 | 1/1981 | Manschot et al. | 422/102 |
| 4,414,705 | 11/1983 | Ostrowsky | 16/225 |
| 4,713,219 | 12/1987 | Gerken et al. | 422/102 |
| 4,718,567 | 1/1988 | LaVange | 215/237 X |
| 5,270,011 | 12/1993 | Altherr | 215/237 X |

Primary Examiner—Jeffrey R. Snay
Attorney, Agent, or Firm—John J. Leavitt

[57] ABSTRACT

Presented is a microtube and closure cap assembly in which the closure cap is flexibly tethered to the microtube so that the closure cap may be swung from a microtube-open position to a microtube-closed and sealed position, and the closure cap then rotated through a predetermined arc to lock the closure cap to the microtube in sealed condition. Opening of the microtube from its sealed and locked condition is effected by reversing the procedure, i.e., rotating the closure cap to unlock it from the microtube and then lifting the closure cap from the microtube to break the seal. A lock lug on the microtube and a lock housing on the closure cap that are initially laterally offset when the microtube is sealed by the closure cap are brought into locking interengagement by relative rotation of the closure cap and microtube following sealing of the microtube.

15 Claims, 3 Drawing Sheets

MICROTUBE HAVING PRESS-TO-SEAL AND TWIST-TO-LOCK CLOSURE CAP

BACKGROUND OF THE INVENTION

1. Field of the Invention

This invention relates to a synthetic resinous microtube having a closed end and an open end, the latter selectively sealable by a digitally manipulable press-to-seal cap structure, and more particularly to a microtube having a cap structure that locks against inadvertent release by twisting (rotation) of the cap structure in relation to the tube after the open end of the tube has been sealed by the press-to-seal cap structure.

2. Description of the Prior Art

The known prior art includes the following United States patents:

| | | |
|---|---|---|
| 3,593,909 | 3,651,992 | 3,986,627 |
| 4,158,902 | 4,209,100 | 4,241,188 |
| 4,244,920 | 4,414,705 | 4,713,219. |

The patents listed do not appear to disclose or even suggest the concept of rotation or twisting of a closure cap in relation to the tube to effect locking thereof following sealing of the tube by the closure cap. Not only is this concept not disclosed or suggested by these patents, additionally, the patents do not appear to disclose structure capable of functioning in the manner indicated.

Accordingly, one of the important objects of the present invention is the provision of a microtube equipped with a closure cap that may be twisted in relation to the microtube to effect positive locking of the closure cap after sealing of the tube.

Another object of the invention is the provision of a microtube equipped with a closure cap in which the closure cap is flexibly tethered to the microtube to enable twisting of the cap when in sealed condition in relation to the microtube to releasably lock the closure cap to the microtube.

A still further object of the invention is the provision of a microtube and closure cap that are integrally tethered together by means enabling twisting of the closure cap in relation to the microtube to lock the closure cap in sealed condition without the tether means imposing a bias to unlock the locked closure cap.

Yet another object of the invention is the provision of a microtube and closure cap assembly that are integral one with the other and which may be injection molded as a unitary structure from suitable synthetic resinous material.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the invention comprises a microtube integral with a closure cap structure enabling digital manipulation of the closure cap into tube-sealed condition without locking the closure cap structure to the microtube, but which optionally enables locking of the closure cap to the microtube by twisting the closure cap after sealing of the microtube opening. Structurally, the microtube presents interiorly an annular seal flange adapted to sealingly impinge the outer periphery of a skirt forming a part of the closure cap, while the closure cap skirt is provided exteriorly with an annular seal adapted to sealingly impinge the inner periphery of the microtube and the annular seal flange of the microtube. Parallel spaced flexible tethers integrally join a peripheral portion of the microtube with an associated peripheral portion of the closure cap to enable digital manipulation of the closure cap in relation to the microtube to insert the skirt of the closure cap into the opening of the microtube to seal the opening. Lock means are provided on the periphery of the closure cap and on the periphery of the microtube normally oriented in circumferentially offset positions to enable sealing of the tube by the closure cap without locking the closure cap to the microtube. The lock means on the periphery of the microtube and the periphery of the closure cap are optionally movable into positive locking interengagement by twisting or rotating the closure cap in relation to the microtube following sealing of the microtube by the closure cap.

All views are greatly enlarged for clarity.

DESCRIPTION OF THE PREFERRED EMBODIMENT

Figure 2:
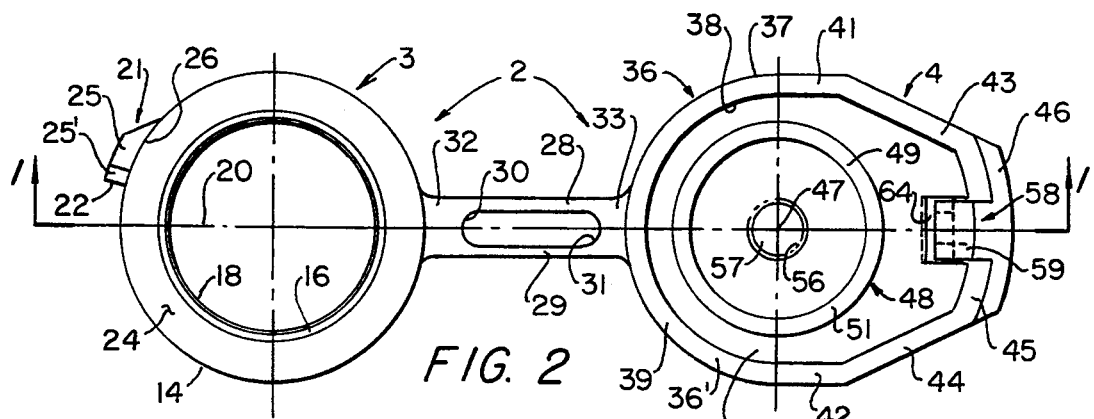
FIG. 2 is a top plan view of the integrally connected microtube and closure cap structure with the closure cap shown in open condition yet flexibly tethered to the microtube.
Figure 1:
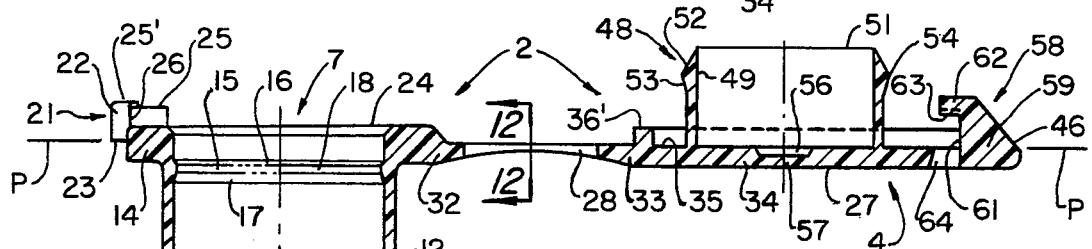
FIG. 1 is an enlarged vertical sectional view taken in the plane indicated by the line 1—1 in FIG. 2.

In terms of greater detail, the microtube of my invention including a press-to-seal and twist-to-lock closure cap is illustrated in FIGS. 1 and 2 in its entirety, and in greater structural detail and different relationships in other views as described above. There has been a long-felt need for a microtube structure such as described and illustrated herein that can withstand the protocols inherent in the medical industry, such as boiling of the microtube, or deep freezing thereof with sample solutions. This latter protocol generally results in known conventional microtubes to pop open when the samples are thawed. It is therefore important that the microtube and closure cap be positively lockable and resist unlocking during such protocols.

Referring to the drawings, it will be seen that the microtube assembly including the closure cap is designated generally by the numeral 2, the microtube per se being designated generally by the numeral 3, while the closure cap tethered integrally to the microtube is designated generally by the numeral 4.

From FIG. 1, it will be seen that the microtube 3 is formed from any of several appropriate synthetic resinous materials, commonly called "plastics", that will withstand the protocols discussed above, and includes an elongated tubular cylindrical body 5 having walls 6 that extend from an open end 7 to a closed end 8. As shown in the drawings, the closed end of the tubular body is conically formed to define a reservoir 9 having a progressively diminishing capacity that is helpful in collecting the last vestige of a liquid sample that is contained in the tube, thus facilitating its removal by aspiration through a syringe needle or pipette. The open end of the tube is defined by a flat annular surface for a purpose which will hereinafter be explained.

The tubular wall 6 possesses an exterior peripheral surface 12, and an interior peripheral surface 13, and at its open end 7 the tubular body is provided with a radially outwardly extending circular flange 14 that projects radially outward beyond the exterior surface of the tube. Additionally, adjacent its open end, the tubular body is also provided with a radially inwardly extending circular seal flange 15 coaxially disposed in relation to the radially outwardly projecting flange 14, but spaced inwardly of the tube from the open end thereof. The flange 15 is formed by two converging annular surfaces 16 and 17 that extend radially inwardly from the interior periphery of the microtube and intercepted by the flat crown 18 of the flange 15 as shown.

It should be noted that the coaxially related outer and inner flanges 14 and 15, respectively, are symmetrical with respect to the longitudinal axis 19 of the tubular body 5. The outer and inner flanges 14 and 15 are also symmetrical in relation to a vertical plane that includes the centerline 20 in FIG. 2, and which plane also includes the longitudinal axis 19 of the tubular body 5 as seen in FIG. 1. Additionally, referring to FIGS. 1, 4, 6, and 9, it should be noted that the seal flange 18 is spaced below the median plane P which is equally spaced between the upper and lower surfaces of the flange 14.

The definitions of these relationships is important for the reason that they help define the location, function, and mode of operation of a lock lug 21 integrally formed on the flange 14 as seen in FIGS. 1, 2, 3, 4, 6 and 9, the lock lug having a front face 22 that lies spaced circumferentially from the centerline 20, with the remainder of the lock lug behind the face 22 extending circumferentially along the outer periphery of the flange 14 in a direction away from the centerline 20. As seen in FIG. 1, the lock lug 21 also includes a lower surface 23 that is spaced substantially medianly on the outer peripheral rim of the flange 14 as shown, i.e., coincident with the plane P, the lower surface 23 of the lug defining a lock engagement surface for a purpose which will hereinafter be explained, and generally following the contour of the remainder of the lock lug as it extends circumferentially on the outer periphery of the flange 14. The lock lug extends upwardly beyond the upper flat surface 24 of the flange 14 as seen in FIG. 1, the surface 24 being parallel to but spaced above the median plane P of the flange 14. The top surface 25 of the lug is provided with an abutment flange 25', and an inner arcuate surface 26 for purposes which will hereinafter be explained.

Figure 3:
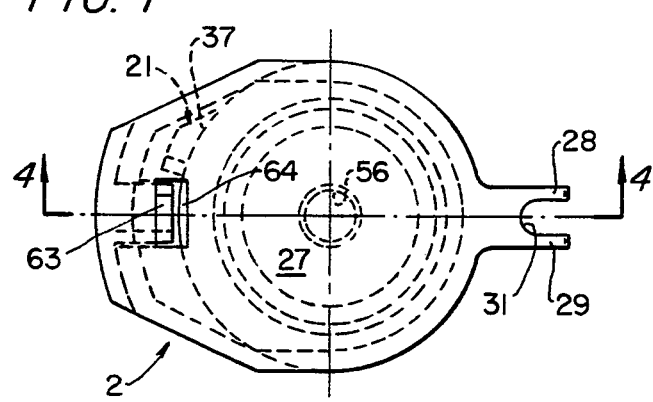
FIG. 3 is a plan view of the microtube and closure cap illustrating the closure cap in tube-sealing but unlocked condition.
Figure 12:
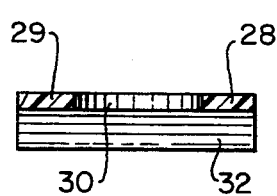
FIG. 12 is an enlarged vertical cross-sectional view of the parallel spaced and flexible tethers integrally joining the microtube and closure cap taken in the plane indicated by the line 12—12 in FIG. 1.
Figure 4:
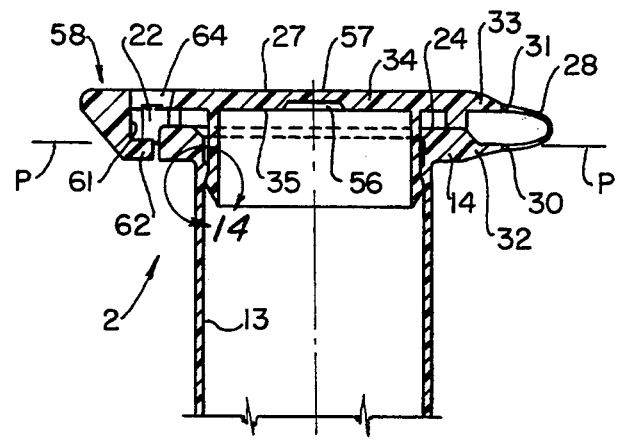
FIG. 4 is a vertical cross-sectional view taken in the plane indicated by the line 4—4 in FIG. 3.
Figure 5:
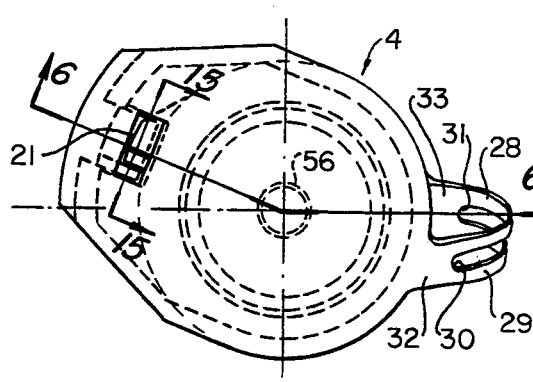
FIG. 5 is a top plan view of the microtube and closure cap illustrating the closure cap in positive locked condition on the microtube.
Figure 7:
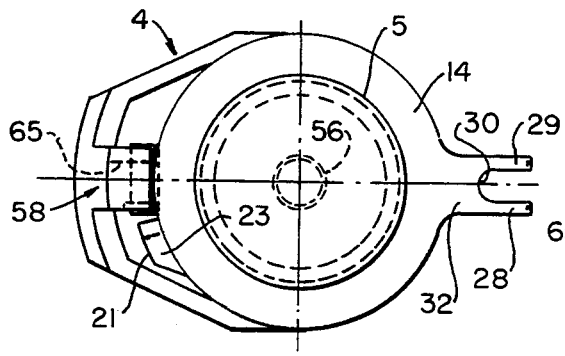
FIG. 7 is a bottom plan view of the microtube and closure cap illustrating the juxtaposed relationship of the locking means when the closure cap is in sealed but unlocked condition in relation to the microtube.

Referring to FIGS. 1 and 2, the microtube 3 and the closure cap 4 are flexibly tethered integrally one to the other to enable the closure cap 4 to be initially repositioned from its open attitude in relation to the microtube 3, as shown in FIGS. 1 and 2, in which the exterior flat surface 27 of the closure cap is coincident with the lower surface of the flange 14 and spaced below the plane P, to a closed and sealed (but not locked) attitude in relation to the microtube 3, as shown in FIGS. 3, 4 and 7. The means by which the microtube 3 and the closure cap 4 are flexibly tethered integrally one to the other includes at least one, but preferably two elongated, juxtaposed and parallel synthetic resinous tethers 28 and 29, opposite ends of which are integrally merged smoothly with the mutually facing ends 30 and 31 of generally rectangular flanges 32 and 33, extending radially and integrally in a common plane, respectively, from the periphery of flange 14 of the microtube and the periphery of the closure cap 4.

It is important to note that the thickness of each tether measured in a median plane intermediate its ends is preferably no thicker than one-half the thickness of the flange with which it merges, say in the order of 0.015 of an inch when the flanges 32 and 33 possess thicknesses in the order of 0.030 of an inch. The thickness and width of the tethers could be diminished to increase their flexibility if that were necessary under special circumstances. It has been determined however that for a microtube having an exterior diameter of approximately 1.1 centimeters and a length of approximately 3.8 centimeters, a tether thickness of 0.015 of an inch and a width one-third, or less, of the width of the flanges 32 and 33, with which its opposite ends are integral, provides sufficient flexibility to accomplish the purpose intended. While the tethers 28 and 29 are illustrated as having arcuate lower surfaces, each having a radius of approximately 0.927 inches, and flat upper surfaces coincident with the plane P, the upper and lower surfaces of the tethers could of course be parallel, or with the upper surfaces arcuate and merged smoothly into the associated flanges 32 and 33.

The flange 33 forms an integral projection from the closure cap 4, which includes a top closure plate 34 of generally uniform thickness corresponding to the thickness of the integral flanges 32 and 33 discussed above. From the surface 35 of the closure plate 34, which is parallel with the top surface 27 of the closure plate, there extends integrally a peripheral flange designated generally by the numeral 36 and having an end surface 36', and inner and outer peripheries 37 and 38, respectively, the outer periphery of which also defines the outer periphery of the closure cap 4. As seen in FIG. 2, a portion 39 of the peripheral flange 36 is semi-circular in configuration, merging smoothly at diametrically spaced locations into parallel flange extensions 41 and 42 spaced equally on opposite sides of a vertical plane that includes the centerline 20. These parallel flange extensions are in turn joined integrally by converging peripheral flange portions 43 and 44, respectively, which converge at an angle of about 25 degrees from the horizontal and which are in turn joined integrally by a circularly arcuate peripheral flange portion 45, chamfered as shown at 46.

The semi-circular portion 39 of the flange 36 on the cover plate 34 is formed coaxially about the axis 47. Also formed on the cover plate 34 coaxially disposed about the axis 47 is a cylindrical tubular skirt designated generally by the numeral 48, and having cylindrical walls 49 integral at one end with the surface 35 of the plate 34. From the surface 35, the tubular skirt 48 extends upwardly as seen in FIGS. 1 and 2 approximately 0.170 of an inch, terminating in an end edge 51 remote from the surface 35 of the cover plate. The outer cylindrical surface of the walls 49 in a region adjacent the end edge 51 is provided with a radially outwardly extending tapered flange formed from converging surfaces 52 and 53 that intercept at a knife-edge seal 54 that circularly circumscribes the outer periphery of the tubular skirt at a point spaced downwardly from the end edge 51.

The converging surface 52 (FIG. 2) is sloped downwardly and outwardly approximately 35 degrees from vertical, while the upwardly converging surface 53 is sloped upwardly and outwardly approximately 15 degrees from vertical. Concentrically formed in the surface 35 of the cover plate 27 at the base or closed end of the skirt is a circular recess 56 the diameter of which is about one-third the interior diameter of the skirt, and the depth of which is about one-half the thickness of the cover plate, thus forming a diaphragm 57 having a thickness of only about 0.015 of an inch or less.

Figure 8:
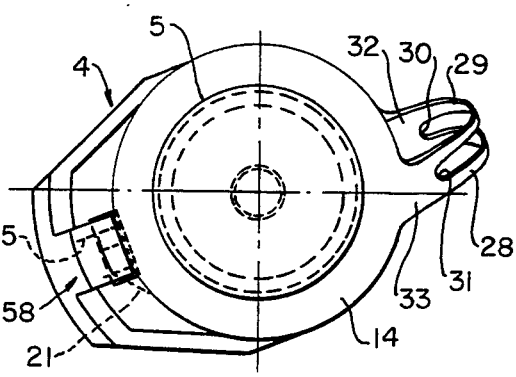
FIG. 8 is a bottom plan view similar to FIG. 7, but illustrating the positive interengaging relationship of the locking means after the sealed closure cap has been twisted or rotated in relation to the microtube to releasably lock the sealed closure cap to the microtube.
Figure 9:
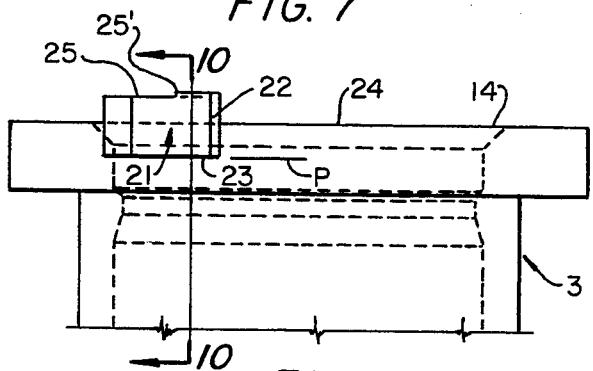
FIG. 9 is an enlarged elevational view of the lock lug formed integrally on the periphery of the microtube, and illustrating also the lock flange that projects above the top surface of the lock lug.
Figure 10:
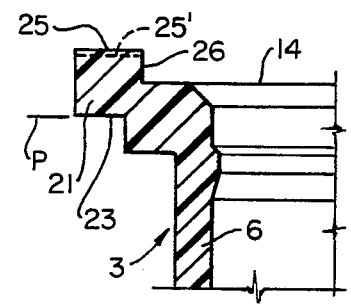
FIG. 10 is an enlarged fragmentary vertical sectional view of the lock lug taken in the plane indicated by the line 10—10 in FIG. 9.
Figure 11:
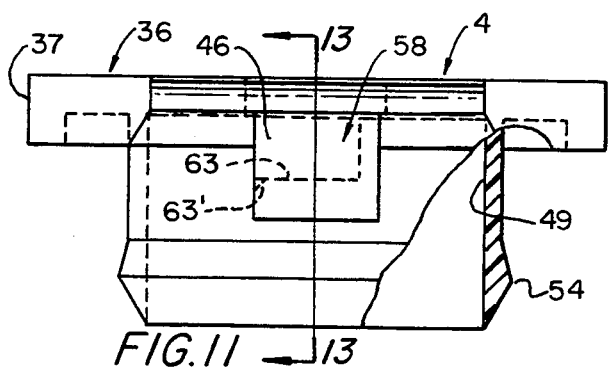
FIG. 11 is an enlarged fragmentary elevational view of the lock formed integrally on the periphery of the closure cap which when the cap is twisted interengages with the lock lug on the rim of the microtube to positively lock the closure cap to the tube.
Figure 13:
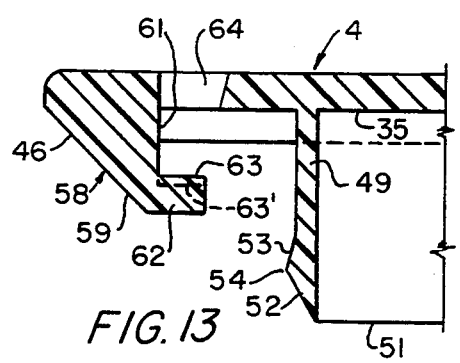
FIG. 13 is a fragmentary vertical cross-sectional view taken in the plane indicated by the line 13—13 in FIG. 11.
Figure 15:
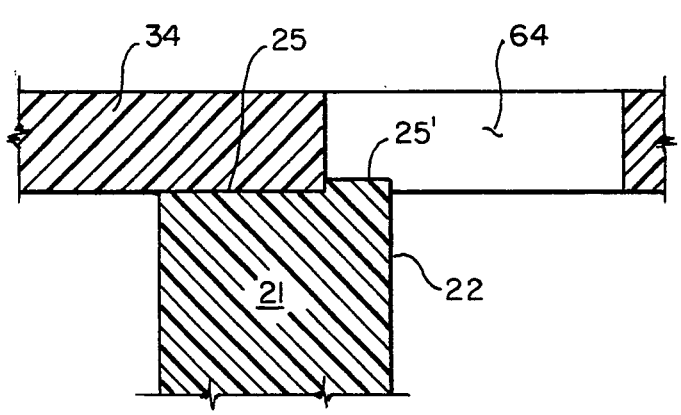
FIG. 15 is an enlarged fragmentary cross-sectional view illustrating the locking relationship between the lock lug and the closure cap.

Referring to FIGS. 1, 2, 3 and 4, it will be seen that formed integrally on the inner surface 35 of the cover plate 27 adjacent the arcuate peripheral flange portion 45 and positioned symmetrically with respect to the center line 20 is a lock housing 58 having a sloping outer surface 59 and an inner surface 61 (FIG. 1) extending vertically from the inner surface 35, and intercepted by an inwardly projecting lock portion 62, the inner surface 63 of which is "ramped" or chamfered at 63' as shown in FIGS. 11 and 13. The inner surface 61 of the lock housing is spaced from the central axis 47 of the closure cap a distance slightly greater than the distance that the outer face of the lock lug 21 is spaced from the central axis 19 of the microtube so that the lock housing may be pivoted circumferentially about the lock lug so that the lock lug is squeezed and confined in the space between the inner surface 35 of the closure plate and the ramped surface 63/63' of the lock housing until pivotal rotation of the closure cap causes the lock flange 25' to "snap" into the aperture 64 formed in the closure plate 27, where it abuts one of the inner end surfaces of the aperture 64 to prevent inadvertent reverse rotation and unlocking of the closure cap from the tube. The elastically resilient displacement of the lock portion 62 by the camming pressure exerted by the lock lug on "ramped" surface 63 aids in retaining the lock flange 25' engaged in the aperture 64 (FIG. 15). An integral wall 65 (FIGS. 7 and 8) formed on the lock housing limits the degree of pivotal rotation of the closure cap in a locking direction by confrontation with front face 22 of the lock lug 21.

Accordingly, when the closure cap is repositioned through flexure of the flexible tethers from its open attitude as seen in FIGS. 1 and 2 to its closed and sealed (but not locked) position illustrated in FIGS. 3 and 4, the ramped surface 63 of the lock portion 62 is in position to be engaged with the lower abutment surface 23 of the lock lug 21, i.e., the surfaces 23 and 63 lie substantially in a common plane, offset only sufficiently to provide an inclined ramp that provides an interference fit between these two surfaces as they are shifted relative to each other to effect positive locking, as will hereinafter be explained.

Figure 6:
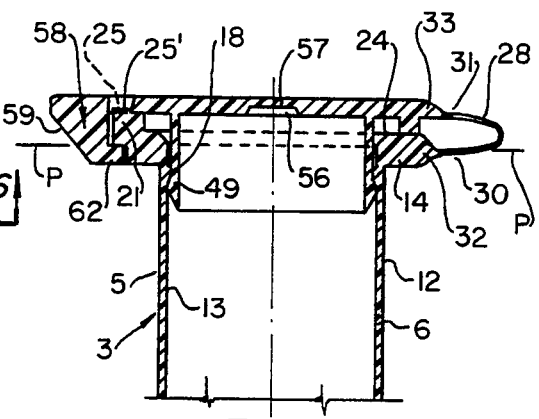
FIG. 6 is a vertical cross-sectional view taken in the plane indicated by the line 6—6 in FIG. 5.
Figure 14:
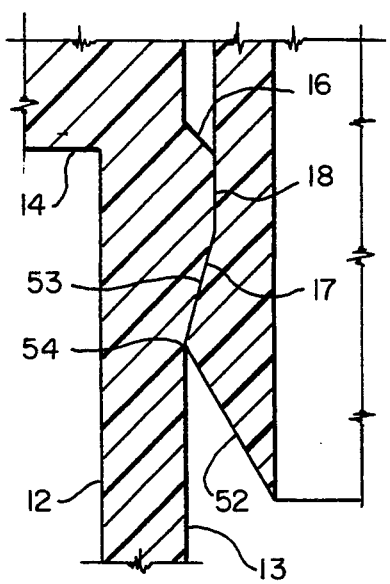
FIG. 14 is an enlarged fragmentary vertical cross-sectional view illustrating the relationships of the sealing surfaces between the closure cap and the interior of the microtube.

Also, in this closed and sealed position of the closure cap, the flat surface 24 of the open end of the microtube is abutted by the end edge 36' of the peripheral flange of the closure cap. Concomitantly, because the tubular skirt 48 when it is repositioned as shown in FIGS. 4 and 6, now extends into the interior of the tubular microtube through its open end 7, seal flange 15 projecting radially into the microtube sealingly abuts the outer periphery of the tubular skirt 48, while simultaneously the knife-edge seal 54 on the tubular skirt 48 sealingly abuts the inner periphery 13 of the microtube body 5. Additionally, the annular tapered surface 17 cooperates with annular tapered surface 53 to ensure the integrity of the seal. These relationships are clearly illustrated in FIGS. 4, 6 and 14 of the drawings and provide three separate and distinct seal locations to prevent leakage of a sample solution or liquid from the microtube. It should also be noted that since the closure cap is positively lockable to the tube and lock lug against opening, internal pressure in the microtube functions to tighten the locked relationship and enhance the seal between the closure cap and tube. Internal pressure in the microtube that tends to lift the closure cap is also effectively resisted by the seal flange 15 acting in concert with the outwardly sloped seal surface 53.

It should be understood that the dimensions of the knife-edge seal 54 on the tubular skirt 48 and the seal flange 15 within the microtube are such that when the closure cap is repositioned over the microtube by pivoting the closure cap counterclockwise as viewed in FIG. 1, the thin flexible tethers flex between their ends to form a substantially semi-circular pattern (FIG. 4), and that a cylindrical peripheral portion of the skirt adjacent its end edge 51 and on the side thereof adjacent the flange 33, dips angularly into the open end of the microtube and past the associated portion of the seal flange 15 before the remainder of the knife-edge seal 54 penetrates the open end of the tube and passes below the seal flange 15 as continued pressure is applied to the cover plate 27 to close the closure plate over the open end 7 of the microtube so that the end edge 36' of the closure cap flange 36 abuts the top surface 24 of the open end of the microtube. In this attitude, the knife-edge seal 54 and seal flange 15 lie in spaced parallel planes that are perpendicular to the central axis 19 of the microtube body 5.

This initial entry of a portion of the cylindrical knife-edge seal 54 angularly into the microtube past the seal flange 15 is facilitated by the relative angles of the converging surfaces that form the knife-edge seal and their relative diameters. Their relative diameters also account for the sealing abutment of the seal surface 18 with the associated exterior surface of the skirt and the abutment of knife-edge seal 54 with the interior surface of the mictrotube to form a very reliable seal between the closure cap and the microtube even in its unlocked yet sealed condition as described above.

To ensure integrity of the seal thus formed between the closure cap and the microtube during a wide range of protocols, it has been determined to be advantageous to positively lock the closure cap to the microtube so as to prevent inadvertent opening of the closure cap. Such positive locking of the closure cap to the microtube is effected by holding the microtube stationary, either by hand or by an appropriate tool, and applying a rotary moment or twisting force clockwise on the closed and sealed closure cap as viewed in FIG. 3. Such a rotary moment may be applied by hand through digital manipulation or by an appropriate tool, and causes the closure plate 27 and the attached skirt 48 to rotate slightly in relation to the microtube, and also results in the inclined or "ramped" surface 63 of the lock portion 62 to slide under the lower surface 23 of the lock lug 21 in an interference fit that imposes a slight elastic flexure on the lock portion 62, a slight compressive force on the lock lug 21, effectively retaining the lock portion surface 63 engaged with the lower surface 23 of the lock lug and causing the abutment flange 25' on the upper surface of the lock lug to "snap" into the aperture 64 and to abut one end thereof to thus reliably restrain the closure cap from rotating counterclockwise, thus retaining the closure cap positively locked in sealed position.

It will thus be seen that with the closure cap thus rotated to interengage the lock lug and its abutment flange 25' with the lock housing and the closure plate aperture 36', it is not normally possible to unlock the closure cap without intentionally and purposefully simultaneously lifting and rotating the closure cap counterclockwise with respect to the microtube to disengage the abutment flange 25' from the aperture 36'. Even when the closure cap is unlocked in this manner, the closure cap still maintains an effective seal with the microtube. To fully open the closure cap, and break the seal, it is necessary to impose an additional lifting force under the arcuate flange portion 45 associated with the lock housing so as to lift the tubular skirt out of the open end of the microtube. Even after the microtube is opened in such manner, the closure cap remains tethered to the microtube by the flexible tethers that integrally join the closure cap to the microtube.

Having thus described the invention, what is believed to be new and novel and sought to be protected by Letters Patent of the United States is as follows.

I claim:

1. A microtube and selectively lockable closure cap assembly, comprising:
  a) a microtube symmetrical about a longitudinal axis and having inner and outer peripheries and open and closed ends, said open end being symmetrical with respect to a plane including said longitudinal axis;
  b) a closure cap symmetrical when in open and in initially closed and sealed positions with respect to said plane including said longitudinal axis and pivotally connected to the open end of the microtube and selectively manipulable between open and closed positions, said closure cap including a tubular cylindrical skirt portion having a seal flange thereon constructed and positioned so as sealingly engage the inner periphery of the microtube to seal the open end thereof when said tubular cylindrical skirt portion is inserted into said open end of the microtube;
  c) a lock lug on said microtube positioned on the open end thereof and offset laterally from said plane that includes said longitudinal axis;
  d) a lock housing on said closure cap symmetrically positioned thereon with respect to said plane that includes said longitudinal axis and laterally offset from said lock lug on said microtube in unlocked position when said closure cap is manipulated into said initially closed and sealed position and selectively laterally movable into interengagement with said lock lug by selective relative rotation of said closure cap and said microtube when in said closed and sealing position; and
  e) means flexibly interconnecting said closure cap and said microtube and enabling said relative rotation of said closed and sealed closure cap in relation to said microtube about the longitudinal axis of said microtube.

2. The combination according to claim 1, wherein said means flexibly interconnecting said closure cap and said microtube comprises at least one flexible tether integrally connected at opposite ends to said closure cap and said microtube, respectively.

3. The combination according to claim 1, wherein said lock housing and said means flexibly interconnecting said closure cap to said microtube are diametrically opposed in relation to the closure cap.

4. The combination according to claim 1, wherein said open end of said microtube is surrounded by a radially outwardly extending flange having an outer periphery, and said lock lug is integrally formed on the outer periphery of said flange.

5. The combination according to claim 4, wherein said radially outwardly extending flange is circularly symmetrical about the longitudinal axis of the microtube, and said lock lug integrally formed on the outer periphry of said flange is offset circumferentially from said plane that includes said longitudinal axis.

6. The combination according to claim 1, wherein said means flexibly interconnecting said closure cap and said microtube comprises a pair of laterally spaced and juxtaposed flexible tethers integrally connected at corresponding opposite ends to said closure cap and said microtube, respectively.

7. The combination according to claim 6, wherein said pair of laterally spaced and juxtaposed flexible tethers vary in thickness from a maximum thickness where corresponding opposite ends are joined integrally to said closure cap and said microtube to a minimum thickness at a plane intermediate said corresponding opposite ends.

8. The combination according to claim 1, wherein said lock lug includes a bottom surface, a top surface and a front surface facing said plane including the longitudinal axis of said microtube, and said lock housing interengages with said lock lug in an interference fit when said closure cap is rotated to engage the lock housing with the lock lug.

9. The combination according to claim 1, wherein said closure cap includes a closure plate having an inner surface, and said lock housing is formed integrally on said inner surface of said closure plate and includes a body portion projecting away from said inner surface and terminating in a lock portion between which and said inner surface of said closure slate said lock lug is engaged in an interference fit when said closure cap is rotated to engage the lock housing with the lock lug.

10. The combination according to claims 1, 8 or 9, wherein said closure cap is provided with an aperture circumferentially aligned with said lock lug, when said lock housing is engaged with said lock lug and said lock is provided with an abutment flange constructed and positioned so as to lockingly engage said aperture in the closure cap when the closure cap is rotated to interengage said lock housing with said lock lug.

11. The combination according to claim 9, wherein said lock portion of said lock housing comprises a flange constructed and positoned so as to engagingly underlie said lock lug when said closure cap is rotated to engage said lock housing with said lock lug and cooperate with said body portion and the inner surface of said closure plate to lockingly enclose said lock lug.

12. The combination according to claim 11, wherein said lock housing is provided with an end wall joining said lock portion, said body portion and said inner surface of said closure plate and constructed and positioned so as to limit the extent of pivotal rotation of said closure cap to only that amount necessary to effectively lock said lock housing to said lock lug when said closure cap is rotated to interengage the lock housing with the lock lug.

13. The combination according to claim 1, wherein the inner periphery of the microtube is provided with a radially inwardly extending annular seal flange integrally formed on the inner periphery of the microtube spaced from said open end of the microtube, and said seal flange on the cylindrical skirt portion of the closure cap sealingly cooperates with said radially inwardly extending annular seal flange on the microtube to seal the open end of the microtube when said closure cap is pivoted into said closed and sealed position.

14. The combination according to claim 13, wherein said radially inwardly extending seal flange integrally formed on the inner periphery of the microtube includes a radially inwardly spaced cylindrical surface coaxially disposed in relation to the inner periphery of the microtube, and at least one annular inclined seal surface diverging from said cylindrical surface to merge integrally with the inner periphery of the microtube.

15. The combination according to claim 14, wherein said cylindrical skirt portion of said closure cap includes an outer periphery, and said seal flange on said cylindrical skirt portion of the closure cap is formed integrally on the outer periphery of the skirt portion and includes a knife-edge seal coaxially spaced about the outer periphery of the cylindrical skirt portion and at least one diverging seal surface that diverges from said knife-edge seal and merges integrally with the outer periphery of the skirt portion, said at least one diverging seal surface of the skirt portion sealingly engaging said at least one diverging seal surface of said seal flange integral with the inner periphery of the microtube when said closure cap is positioned in said closed and sealed position.

* * * * *